(12) United States Patent
Wang et al.

(10) Patent No.: US 8,142,052 B2
(45) Date of Patent: Mar. 27, 2012

(54) MEDICAL LIGHT SOLIDIFYING DEVICE

(75) Inventors: Shan-Non Wang, Jhongli (TW); Shih-Chi Ou, Sansia Township, Taipei County (TW); Chia-Ming Chang, Taoyuan (TW)

(73) Assignee: Rolence Enterprise Inc., Taoyuan County (TW)

( * ) Notice: Subject to any disclaimer, the term of this patent is extended or adjusted under 35 U.S.C. 154(b) by 448 days.

(21) Appl. No.: 12/419,406

(22) Filed: Apr. 7, 2009

(65) Prior Publication Data
US 2010/0252753 A1   Oct. 7, 2010

(51) Int. Cl.
*F21V 21/00* (2006.01)
*F21V 7/00* (2006.01)

(52) U.S. Cl. .......... 362/249.06; 362/297; 362/346; 362/373; 250/504 R; 250/495.1

(58) Field of Classification Search ........... 362/33, 362/92, 230, 234, 241, 247, 249.02, 249.06, 362/249.14, 346, 294, 373, 297; 250/503.1, 250/492.1, 504 R, 494.1, 495.1
See application file for complete search history.

(56) References Cited

U.S. PATENT DOCUMENTS

| | | | | |
|---|---|---|---|---|
| 4,546,261 A * | 10/1985 | Gonser et al. | | 250/492.1 |
| 4,771,154 A * | 9/1988 | Bell et al. | | 219/685 |
| 5,298,758 A * | 3/1994 | Tateosian et al. | | 250/492.1 |
| 5,477,054 A * | 12/1995 | Tateosian et al. | | 250/492.1 |
| 5,721,805 A * | 2/1998 | Cook et al. | | 392/411 |
| 6,448,540 B1 * | 9/2002 | Braunisch et al. | | 219/685 |
| 6,818,864 B2 * | 11/2004 | Ptak | | 219/390 |
| 7,323,663 B2 * | 1/2008 | Cavada et al. | | 219/411 |

* cited by examiner

*Primary Examiner* — Thomas Sember
(74) *Attorney, Agent, or Firm* — Kile Goekjian Reed & McManus PLLC

(57) ABSTRACT

A medical light solidifying device includes a housing box, a rotary work table, a lighting source reflection body, and an LED lighting source set. The rotary work table is rotatably located in the housing box for being placed with a target material. The lighting source reflection body includes at least two reflection masks. Each mask has a reflection wall surrounding the rotary work table. Each of the reflection walls of the two reflection masks respectively has at least one reflection surface. The LED lighting source set is located above the rotary work table and the lighting source reflection body, and includes a plurality of LED units for emitting a beam with a specific wavelength for solidifying the target material. Thereby, the dead zone of the LED lighting source set is reduced so that the usage efficiency thereof is increase, and furthermore the target material can be efficiently and uniformly solidified.

15 Claims, 7 Drawing Sheets

MEDICAL LIGHT SOLIDIFYING DEVICE

BACKGROUND OF THE INVENTION

1. Field of the Invention

The present invention relates to a medical light solidifying device; in particular, the present invention relates to a medical light solidifying device that utilizes a light beam with a specific wavelength emitted from an LED unit so as to solidify a target material.

2. Description of Related Art

A medical light solidifying device for the dental artisan utilizes a light beam to solidify a target material, such as a tooth mold, or an artificial tooth, wherein the production process is complex. However, the lighting source for a traditional medical light solidifying device, such as halogen lamp, merely emits light beam from a single light source location. Thus the target material that has been solidified may not be uniform. Therefore, a rotary work table is used for changing the following conditions so as to rapidly and uniformly solidify the target material.

1. Shortens the distance between the lighting source and the target material.
2. Increases the light intensity of the lighting source.
3. Changes the location of the lighting source.

However, the medical light solidifying device of the prior art still has the following problems.

1. If the distance between the lighting source and the target material is shortened, it is then inconvenient to take or place the target material.
2. If the light intensity of the lighting source is increased, the target material may still not be uniformly solidified due to the outline of the target material not being a single surface, so that the lighting source cannot uniformly emit upon all surfaces, or in order to cover all surfaces the lighting source may have to be moved to various locations and thereby taking more time.
3. If the location of the lighting source has been changed, the location of the target material being emitting is consequently changed. However, because the outline of the target material is not a single surface, a dead zone may exist so that the target material may still not be uniformly solidified even by change the location of the lighting source.

SUMMARY OF THE INVENTION

One particular aspect of the present invention is to provide a medical light solidifying device that utilizes an LED lighting source set, a lighting source reflection body, and a rotary work table so as to efficiently use the light beam emitted from an LED unit in order to improve the solidified uniformity of a target material and improved the solidifying efficiency thereof.

The medical light solidifying device includes a housing box, a rotary work table, a lighting source reflection body, and an LED lighting source set. The rotary work table is rotatably located in the housing box. The lighting source reflection body includes at least two reflection masks. Each mask has a reflection wall. The reflection walls of the two reflection masks surrounds around the rotary work table One side of the reflection walls of the two reflection masks that is close to the rotary work table respectively has at least one reflection surface. The reflection surfaces of the two reflection masks form a light shining space. The LED lighting source set is located above the rotary work table and the lighting source reflection body. The LED lighting source set includes a plurality of LED units that are disposed at intervals.

The present invention has the following characteristics. The present invention can reduce the emitting dead zone of the LED lighting source set so as to increase the efficiency of the LED lighting source set. Furthermore, by efficiently rotating the rotary work table, the target material can be efficiently and uniformly solidified.

For further understanding of the present invention, reference is made to the following detailed description illustrating the embodiments and examples of the present invention. The description is for illustrative purpose only and is not intended to limit the scope of the claim.

DETAILED DESCRIPTION OF THE PREFERRED EMBODIMENTS

Figure 1:
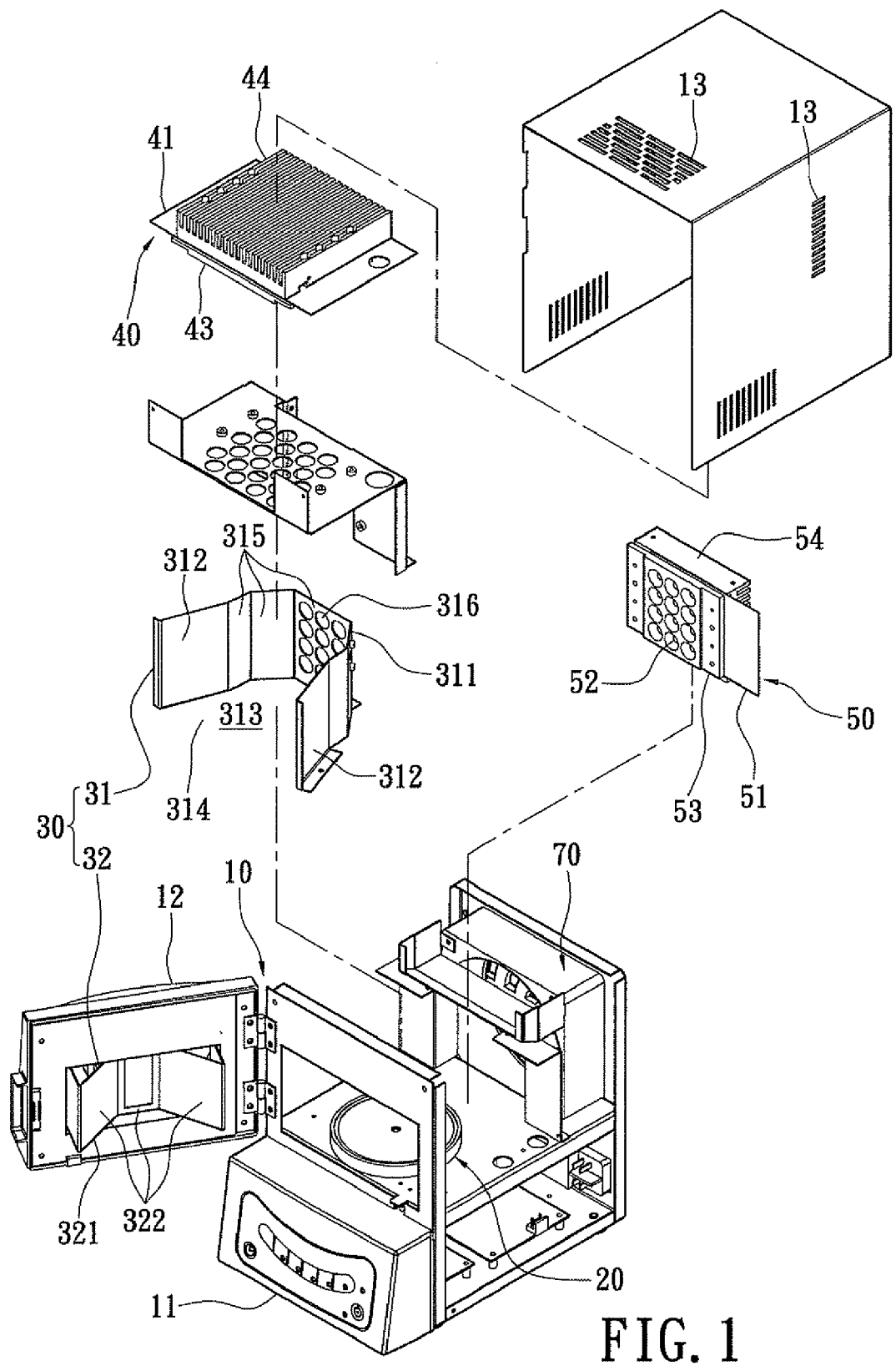
FIG. 1 is an exploded perspective view of a medical light solidifying device of the present invention.
Figure 2:
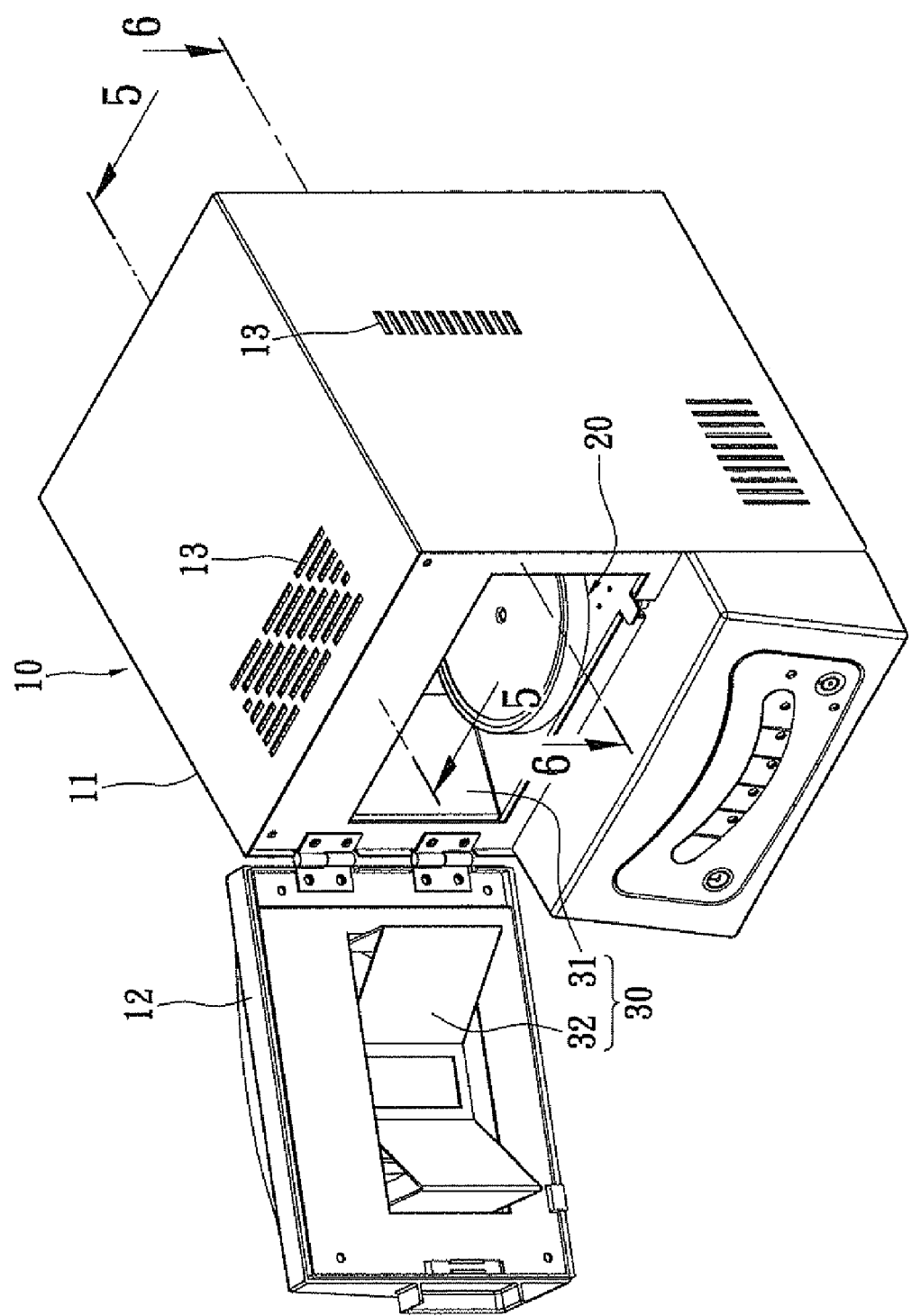
FIG. 2 is an assembly perspective view of the medical light solidifying device of the present invention.
Figure 3:
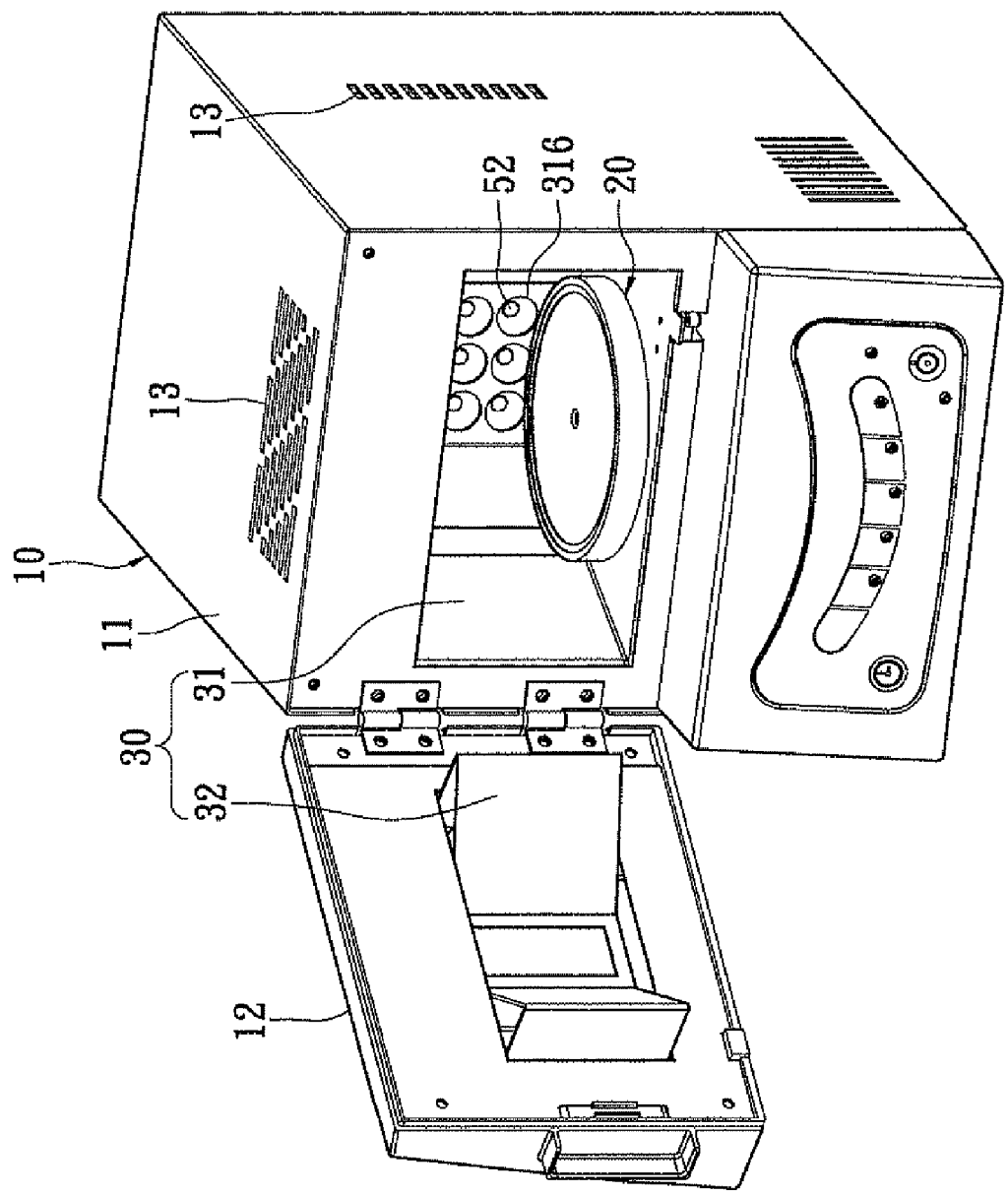
FIG. 3 is another assembly perspective view of the medical light solidifying device of the present invention.
Figure 4:
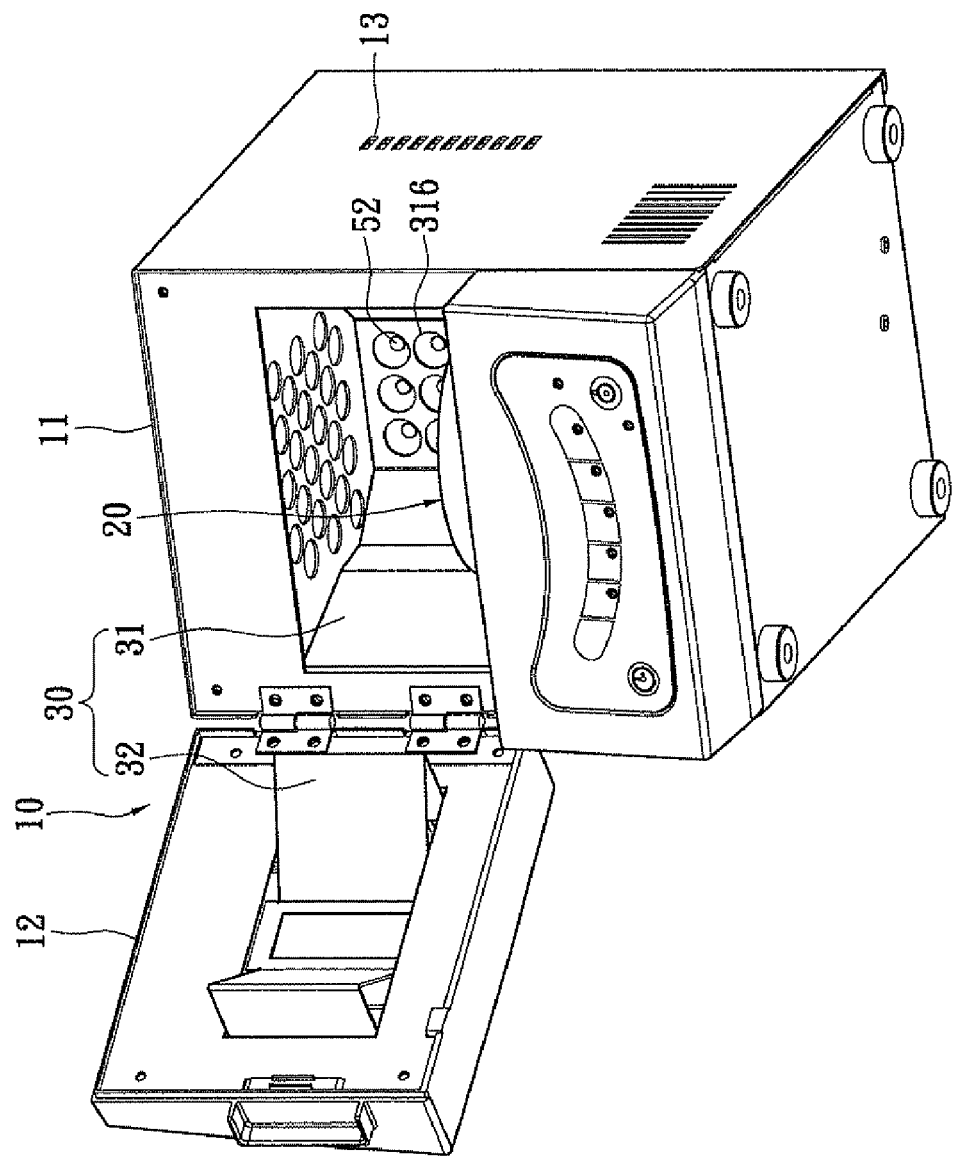
FIG. 4 is a further assembly perspective view of the medical light solidifying device of the present invention.

Reference is made to FIGS. 1, 2, 3, and 4. The medical light solidifying device includes a housing box 10, a rotary work table 20, a light source reflection body 30, and a first LED light source set 40.

The housing box 10 includes a box body 11 and a box door 12. There is a plurality of cooling holes 13 on the two sides of the box body 11 and upper side of the box body 11. The box door 12 is combined with the box body 11 and can be opened and closed. The rotary work table 20 can be circular or polygonal for being placed with a target material (not shown in the figure), such as a tooth mold or an artificial tooth. The rotary work table 20 is rotatably located in the housing box 10. The rotary work table 20 also is linked with a power device 60 for driving the rotary work table 20. The power device 60 can be a motor, but is not limited to only being a motor. In this embodiment, the power device 60 is located in the housing box 10 and below the rotary work table 20.

The light source reflection body 30 includes at least two reflection masks 31, 32, including a first reflection mask 31 and a second reflection mask 32. The first reflection mask 31 has a first reflection wall 311. Two sides of the first reflection wall 311 respectively and slantedly extend forwards to form a slant wall 312. Between the two slant walls 312, an opening portion 313 is formed and is gradually wider from the rear side to the front side. The front side of the two slant walls 312 forms an opening 314. The second reflection mask 32 has a second reflection wall 321 that corresponds to the first reflection wall 311.

The first reflection mask 31 is located in the box body 11 of the housing box 10. The second reflection mask 32 is located at one side of the box door 12 and is adjacent to the box body 11. Thereby, when the box door 12 is closed, the second reflection mask 32 is located before the first reflection mask 31, and the second reflection wall 321 extends into the opening portion 313 of the first reflection mask 31 via the opening 314 so that the first reflection wall 311 of the first reflection mask 31 and the second reflection wall 321 of the second reflection mask 32 surround around the rotary work table 20.

One side of the first reflection wall 311 of the first reflection mask 31 and the second reflection wall 321 of the second reflection mask 32 that is adjacent to the rotary work table 20 respectively has at least one first reflection surface 315 and at least one second reflection surface 322. The first reflection surface 315 and the second reflection surface 322 form a light shining space 33 (referring to FIG. 7). However, the shape of the cross-section of the light shining space 33 is not limited to a specific one, and can be polygonal, circular, or elliptic that can focus the light beam. In this embodiment, the quantity of the first reflection surface 315 is five and the first reflection surfaces 315 are connected, and the quantity of the second reflection surface 322 is three, and the second reflection surfaces 322 are connected. Therefore, the cross-section of the light shining space 33 is octagon.

Alternatively, the first reflection mask 31 merely has one first reflection surface 315 (not shown in the figure) with a semi-arc shape (or semi-elliptic arc shape), and the second reflection mask 32 merely has one second reflection surface 322 (not shown in the figure) with a semi-arc shape (or semi-elliptic arc shape) so that the cross-section of the light shining space 33 is circular (or elliptic).

Furthermore, the material and the working process for the first reflection surface 315 and the second reflection surface 322 is not limited to a specific one, and the working process can be a chromate treatment process, a polishing process, or an anode process, etc.

Figure 5:
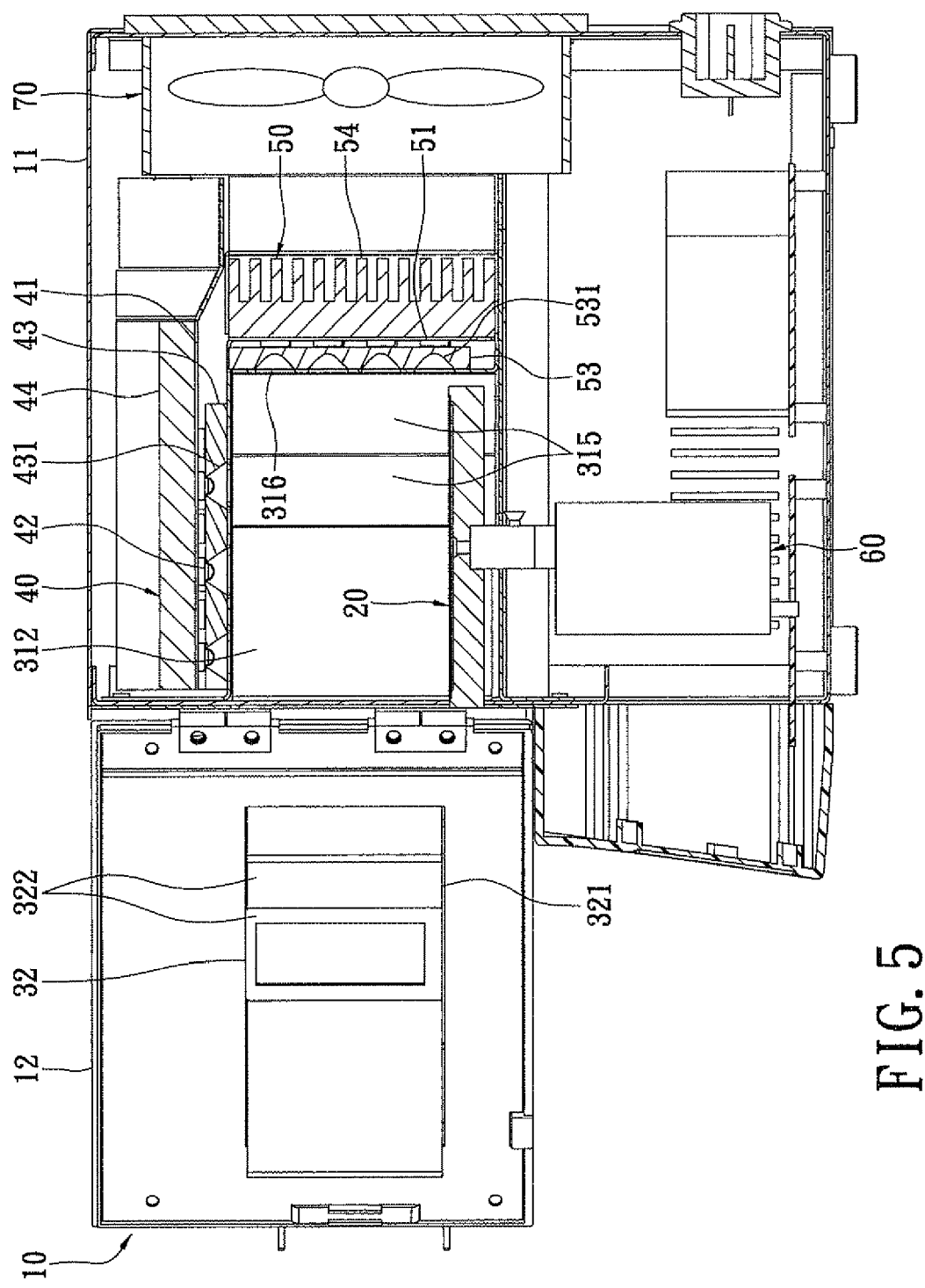
FIG. 5 is a cross-sectional diagram of the cross-section 5-5 in FIG. 2.

Reference is made to FIG. 5. The first LED light source set 40 is located above the rotary work table 20 and the light source reflection body 30 for emitting a light beam with a specific wavelength so as to solidify the target material. The first LED light source set 40 includes a first circuit board 41, a plurality of first LED units 42 disposed at intervals, a first lamp mask 43, and a first cooler 44.

The first LED units 42 are located at one side of the first circuit board 4 1. The first LED units 42 emit a light beam with a specific wavelength to solidify the target material. The disposition way and the quantity of the first LED units 42 is not limited to a specific one.

The first lamp mask 43 covers the first LED units 42 and has a plurality of first reflection portions 431 that correspond to the first LED units 42 for focusing the light beam emitted from the first LED units 42. The first cooler 44 is pasted and located at another side of the first circuit board 41 for absorbing and exhausting the heat generated from the first LED units 42.

Figure 6:
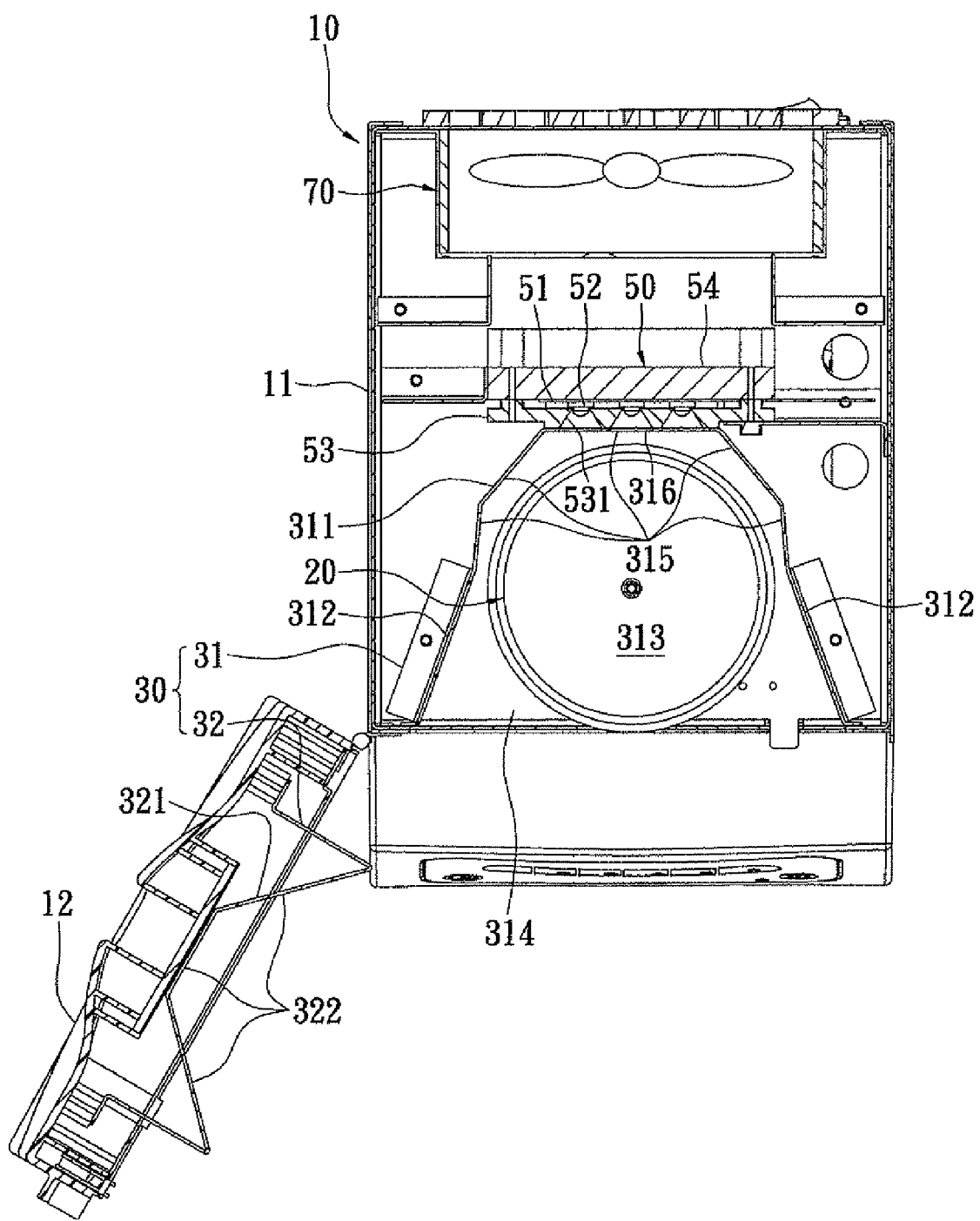
FIG. 6 is a cross-sectional diagram of the cross-section 6-6 in FIG. 2.
Figure 7:
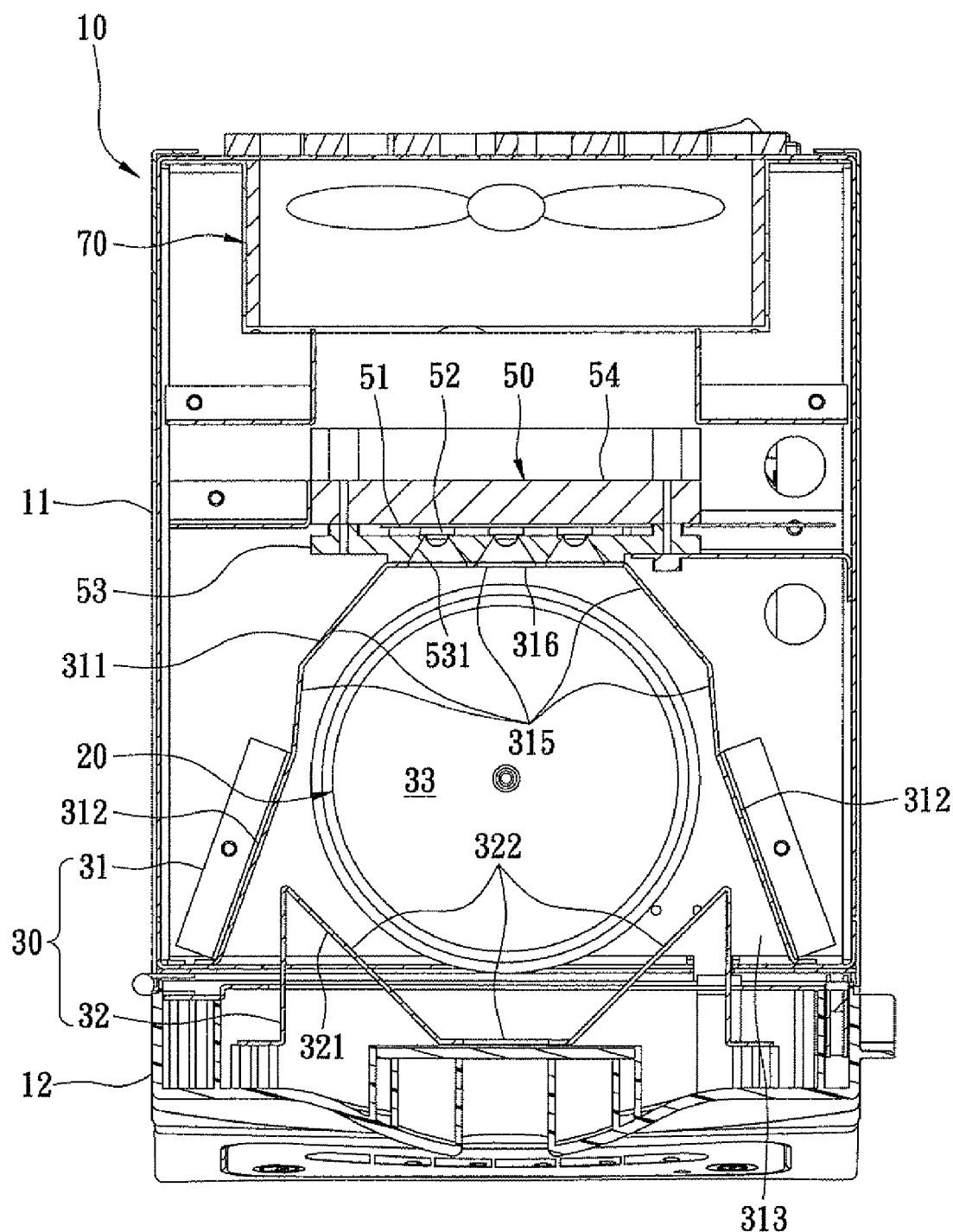
FIG. 7 is a cross-sectional diagram of the housing box in FIG. 6 being closed.

Reference is made to FIGS. 6 and 7. When the present invention is operated, the target material is placed on the rotary work table 20. Because the front side of the first reflection mask 31 has the opening 314 and the opening portion 313 is gradually wider from the rear side to the front side, it is convenient for the operator to take and place the target material.

After the box door 12 is closed, the second reflection wall 321 of the second reflection mask 32 extends into the opening portion 313 of the first reflection mask 31 via the opening 314 so that the first reflection wall 311 and the second reflection wall 321 surrounds around the rotary work table 20. Moreover, because the first reflection surface 315 and the second reflection surface 322 form a smaller light shining space 33, the reflection surfaces 315, 322 is closer to the target material. Next, utilizing the light beam of the first LED unit 41 of the first LED light source set 40 and the light beam reflected from the reflection surfaces 315, 322 to shine upon all surfaces of the target material and rotating the rotary work table 20, the target material is solidified. Thereby, the light beam is focused, the target material is efficiently and uniformly solidified, and the light beam is fully utilized.

Reference is made to FIGS. 1-7. The medical light solidifying device further includes a second LED light source set 50 and a cooling fan 70. The second LED light source set 50 is located at one side of the first reflection wall 311 of the first reflection mask 31. The second LED light source set 50 includes a second circuit board 51, a plurality of second LED units 52 disposed at intervals, a second lamp mask 53, and a second cooler 54.

The second LED units 52 are located at one side of the second circuit board 51. The second LED units 52 emit a light beam with a specific wavelength to solidify the target material. The disposition way and the quantity of the second LED units 52 are not limited to a specific one. The second lamp mask 53 covers the second LED units 52 and has a plurality of second reflection portions 531 that correspond to the second LED units 52 for focusing the light beam emitted from the second LED units 52. The second cooler 54 is pasted and located at another side of the second circuit board 51 for absorbing and exhausting the heat generated from the second LED units 52. The first reflection mask 31 has a plurality of through holes 316 that correspond to the second LED units 52 for emitting the light beam of the second LED units 52. Thereby, a plurality of light sources with different locations is provided to reduce the dead zone and furthermore to improve solidifying efficiency and uniform degree of the target material.

The cooling fan 70 is located in the housing box 10 and is adjacent to the rear side of the second LED light source set 50 for exhausting the heat of the first LED light source set 40 and the second LED light source set 50 via the cooling holes 13 located on the two sides and the upper side of the housing box 10.

The medical light solidifying device of the present invention has the following characteristics.

1. The light source reflection body includes at least two reflection masks respectively located at the box body and the box door. Each of the reflection masks has a reflection wall that is located at the front side of the reflection mask of the box body to form an opening and an opening portion that is gradually wider from the rear side to the front side. Therefore, the opening is wide enough to take and place the target material. After the box door is closed, the reflection wall of the reflection mask of the box door extends into the opening portion of the reflection mask of the box body to from a smaller light shining space with the reflection wall of the reflection mask of the box body. Therefore, each of the reflection surfaces is closer to the target material so that the light beam is efficiently reflected around the target material.

2. The light source of the present invention is not limited to a single location. According to the design or requirement, the locations of the light sources can be multiple. Even though the illumination of the LED light source sets is weaker than the traditional light sources, the uniform of the illumination is improved, the circuit is simplified, and the cooling design for LED units is simplified. Thereby, the target material is uniformly solidified, and the drawback of the illumination of the light source being enhanced but cannot shine upon each surface of the target material is improved.

3. The rotary work table can be rotated according to the required rotation speed, and cooperates with the light source reflection body and the LED light source set so as to reduce the light shining dead zone. Thereby, the target material can be efficiently and uniformly solidified.

The description above only illustrates specific embodiments and examples of the present invention. The present invention should therefore cover various modifications and variations made to the herein-described structure and operations of the present invention, provided they fall within the scope of the present invention as defined in the following appended claims.

What is claimed is:

1. A medical light solidifying device, comprising:
a housing box;
a rotary work table rotatably located in the housing box;
a lighting source reflection body including at least two reflection masks, wherein each mask has a reflection wall, the reflection walls of the two reflection masks surrounds around the rotary work table, one side of the reflection walls of the two reflection masks that is close to the rotary work table respectively has at least one reflection surface, and the reflection surfaces of the two reflection masks form a light shining space; and
an LED light source set located above the rotary work table and the lighting source reflection body, wherein the LED light source set includes a plurality of LED units that are disposed at intervals;
wherein the two reflection masks are a first reflection mask and a second reflection mask, the second reflection is located before the first reflection mask, two sides of the reflection wall of the first reflection mask respectively and slantedly extends forwards to form a slant wall, an opening portion that is gradually wider form the rear side to the front side is formed between the two slant walls, the front side of the two slant walls has an opening, and the reflection wall of the second reflection mask extends into the opening portion of the first reflection mask via the opening.

2. The medical light solidifying device as claimed in claim 1, wherein the rotary work table is linked with a power device for driving the rotary work table.

3. The medical light solidifying device as claimed in claim 1, wherein the hosing box includes a box body and a box door combined with the box body that can be opened and closed, the first reflection mask is located in the box body, and the second reflection mask is located at one side of the box door that is adjacent to the box body.

4. The medical light solidifying device as claimed in claim 1, wherein the cross-section of the light shining space is polygonal, circular, or elliptic.

5. The medical light solidifying device as claimed in claim 1, further comprising another LED light source set, wherein the another LED light source set is located at one side of reflection wall of one of the reflection masks, and the another LED light source set includes a plurality of another LED units that are disposed at intervals.

6. The medical light solidifying device as claimed in claim 5, wherein the another LED light source set further comprises a circuit board, a lamp mask, and a cooler, the another LED units are located at one side of the circuit board, one of the reflection masks has a plurality of through holes that correspond to the another LED units, the lamp mask covers the another LED units and has a plurality of reflection portions that correspond to the another LED units, and the cooler is pasted and located at another side of the circuit board.

7. The medical light solidifying device as claimed in claim 1, wherein the cross-section of the light shining space is polygonal, circular, or elliptic.

8. The medical light solidifying device as claimed in claim 1, further comprising another LED light source set, wherein the another LED light source set is located at one side of reflection wall of one of the reflection masks, and the another LED light source set includes a plurality of another LED units that are disposed at intervals.

9. The medical light solidifying device as claimed in claim 8, wherein the another LED light source set further comprises a circuit board, a lamp mask, and a cooler, the another LED units are located at one side of the circuit board, one of the reflection masks has a plurality of through holes that correspond to the another LED units, the lamp mask covers the another LED units and has a plurality of reflection portions that correspond to the another LED units, and the cooler is pasted and located at another side of the circuit board.

10. The medical light solidifying device as claimed in claim 1, wherein the reflection surface of the reflection mask is processed by a chromate treatment process, a polishing process, or an anode process.

11. The medical light solidifying device as claimed in claim 1, wherein the LED light source set further comprises a circuit board, a lamp mask, and a cooler, the LED units are located at one side of the circuit board, the lamp mask covers the LED units and has a plurality of reflection portions that correspond to the LED units, and the cooler is pasted and located at another side of the circuit board.

12. The medical light solidifying device as claimed in claim 1, further comprising a cooling fan, wherein the cooling fan is located in the housing box.

13. The medical light solidifying device as claimed in claim 1, wherein the rotary work table is circular or polygonal.

14. A medical light solidifying device, comprising:
a housing box;
a rotary work table rotatably located in the housing box;
a lighting source reflection body including at least two reflection masks, wherein each mask has a reflection wall, the reflection walls of the two reflection masks surrounds around the rotary work table, one side of the reflection walls of the two reflection masks that is close to the rotary work table respectively has at least one reflection surface, and the reflection surfaces of the two reflection masks form a light shining space; and
a first and a second LED light sources, wherein the first LED light source set is located above the rotary work table and the lighting source reflection body, and includes a plurality of first LED units that are disposed at intervals; wherein the second LED light source set is located at one side of reflection wall of one of the reflection masks, and includes a plurality of second LED units that are disposed at intervals;
wherein the second LED light source set further comprises a circuit board, a lamp mask, and a cooler, the second LED units are located at one side of the circuit board, one of the reflection masks has a plurality of through holes that correspond to the second LED units, the lamp mask covers the second LED units and has a plurality of reflection portions that correspond to the second LED units, and the cooler is pasted and located at another side of the circuit board.

15. A medical light solidifying device, comprising:
a housing box;
a rotary work table rotatably located in the housing box;
a lighting source reflection body including at least two reflection masks, wherein each mask has a reflection wall, the reflection walls of the two reflection masks surrounds around the rotary work table, one side of the reflection walls of the two reflection masks that is close to the rotary work table respectively has at least one reflection surface, and the reflection surfaces of the two reflection masks form a light shining space; and an LED light source set located above the rotary work table and the lighting source reflection body, wherein the LED light source set includes a plurality of LED units that are disposed at intervals;

wherein the LED light source set further comprises a circuit board, a lamp mask, and a cooler, the LED units are located at one side of the circuit board, the lamp mask covers the LED units and has a plurality of reflection portions that correspond to the LED units, and the cooler is pasted and located at another side of the circuit board.

* * * * *